(12) United States Patent
Everman et al.

(10) Patent No.: US 12,396,669 B2
(45) Date of Patent: Aug. 26, 2025

(54) APPARATUSES AND METHOD FOR GAUGING THE EFFECT OF EXTERNAL FACTORS RELATING TO A USER COGNITIVE PERFORMANCE

(71) Applicant: GMECI, LLC, Beavercreek, OH (US)

(72) Inventors: Bradford Everman, Haddonfield, NJ (US); Brian Bradke, Brookfield, VT (US)

(*) Notice: Subject to any disclaimer, the term of this patent is extended or adjusted under 35 U.S.C. 154(b) by 53 days.

(21) Appl. No.: 17/959,569

(22) Filed: Oct. 4, 2022

(65) Prior Publication Data

US 2024/0108261 A1 Apr. 4, 2024

(51) Int. Cl.
*A61B 5/00* (2006.01)
*A61B 5/16* (2006.01)

(52) U.S. Cl.
CPC .............. *A61B 5/165* (2013.01); *A61B 5/163* (2017.08); *A61B 5/7267* (2013.01); *A61B 5/746* (2013.01)

(58) Field of Classification Search
None
See application file for complete search history.

(56) References Cited

U.S. PATENT DOCUMENTS

| 10,561,863 | B1 | 2/2020 | Dashevsky |
| 2013/0246088 | A1* | 9/2013 | Huster ............... G06Q 10/0635 705/2 |
| 2017/0347906 | A1* | 12/2017 | Intrator ............... A61B 5/7264 |
| 2019/0061772 | A1 | 2/2019 | Prinz |
| 2021/0217532 | A1* | 7/2021 | Heimerl .................. A61B 5/11 |
| 2022/0043404 | A1* | 2/2022 | Fukui ..................... A61B 5/165 |

FOREIGN PATENT DOCUMENTS

WO 2021/222155 A1 11/2021

* cited by examiner

*Primary Examiner* — Sana Sahand
(74) *Attorney, Agent, or Firm* — Caldwell Intellectual Property Law

(57) ABSTRACT

An apparatus and method for gauging the effect of external factors relating to a user cognitive performance. The apparatus includes a plurality of sensors configured to detect at least a physiological parameter and an environmental parameter, at least a processor, and a memory communicatively connected to the at least a processor, the memory containing instructions configuring the at least a processor to receive physiological feedback from the plurality of sensors, receive environmental feedback from the plurality of sensors, generate an external factor profile containing a plurality of external factors selected by the processor configured to improve the user cognitive performance as a function of the received biological feedback and environmental feedback.

18 Claims, 7 Drawing Sheets

APPARATUSES AND METHOD FOR GAUGING THE EFFECT OF EXTERNAL FACTORS RELATING TO A USER COGNITIVE PERFORMANCE

FIELD OF THE INVENTION

The present invention generally relates to the field cognitive performance. In particular, the present invention is directed to apparatuses and method for gauging the effect of external factors relating to a user cognitive performance.

BACKGROUND

Current methods of analyzing and improving user cognitive performance are insufficient. There is a need for identifying the effects external factors have on user cognitive performance.

SUMMARY OF THE DISCLOSURE

In an aspect an apparatus for gauging the effect of external factors relating to a user cognitive performance. The apparatus includes a plurality of sensors configured to detect at least a physiological parameter and an environmental parameter, at least a processor, and a memory communicatively connected to the at least a processor, the memory containing instructions configuring the at least a processor to receive physiological feedback from the plurality of sensors, receive environmental feedback from the plurality of sensors, generate an external factor profile containing a plurality of external factors selected by the processor configured to improve the user cognitive performance as a function of the received biological feedback and environmental feedback.

In another aspect a method for gauging the effect of external factors relating to a user cognitive performance, the method including receiving, by a processor, from a plurality of sensors configured to detect at least a physiological parameter and an environmental parameter physiological feedback, environmental feedback, and generating, by the processor, an external factor profile containing a plurality of external factors selected by the processor configured to improve the user cognitive performance as a function of the received biological feedback and environmental feedback.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for gauging the effect of external factors relating to a user cognitive performance. In an embodiment, apparatuses and methods disclosed herein may be used to determine a cognitive status of a user.

Aspects of the present disclosure can be used to alert a user and third parties of external factors actively affecting user cognitive performance Aspects of the present disclosure can also be used to alert a user or third of a poor cognitive status of a user.

Exemplary embodiments illustrating aspects of the present disclosure are described below in the context of several specific examples.

Figure 1:
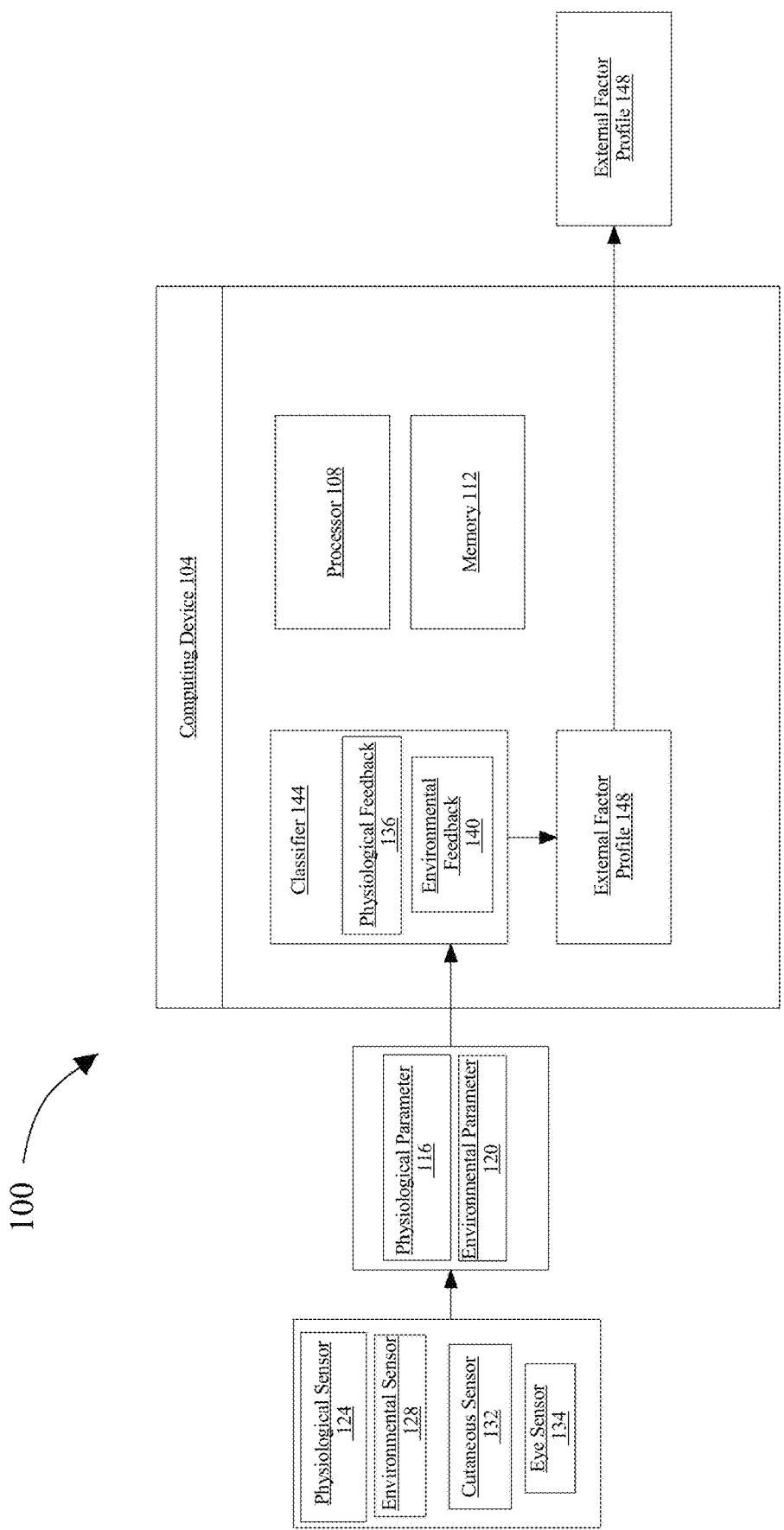
FIG. 1 is an exemplary embodiment of an apparatus for gauging the effect of external factors relating to a user cognitive performance.

Referring now to FIG. 1, an exemplary embodiment of an apparatus 100 for gauging the effect of external factors relating to a user cognitive performance is illustrated. Apparatus may include a computing device 104. Computing device 104 includes a processor 108 and a memory 112 communicatively connected to the processor 108, wherein memory 112 contains instructions configuring processor 108 to carry out the gauging process. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory 112 between computing devices. computing device 104 may be implemented using a "shared nothing" architecture in which data is cached at the worker, in an embodiment, this may enable scalability of apparatus 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1. apparatus includes a plurality of sensors configured to detect at least a physiological parameter 116 and environmental parameter 120. As used in the current disclosure, a "physiological parameter" includes detection of any datum describing a physiological state of user. As used in the current disclosure, a "physiological state" is a physical condition associated with the user. The Physiological state may be associated with a data element describing the users physical or mental health. A "environmental parameter," as used in this disclosure, is a detected environmental condition. At least an environmental parameter 120 may include one or more parameters that can affect sensor readings, such as humidity, temperature, and/or air pressure. Apparats may include environmental sensor 128. As used in this disclosure, a "sensor" is a device that is configured to detect information as a function of a phenomenon; in some cases, a sensor may also transmit the detected information. Environmental sensors 128 may include environmental gas flow sensors, environmental gas pressure sensors, environmental gas temperature sensors, environmental gas humidity sensors, environmental gas concentration sensors, inertial measurement units (IMUs), and the like. At least an environmental parameter 120 may be any parameter and/or combination of parameters detectable by an environmental sensor 128. Sensor may self-correct for variation in such environmental parameters 120 if the environmental parameters 120 are input to sensor; alternatively or additionally, processor 108 may use different calibration settings for different levels of environmental parameters 120 and/or combinations thereof; such levels may be set in a test facility and/or measured in combination with sensor outputs and known levels of substances to be sensed. Processor 108 may compare at least an environmental parameter 120 to one or more values and/or ranges of values to determine which calibration setting to use. Thus, for instance, a first calibration setting may be used for a pressure of approximately 1 atm, a relative humidity level of 30%, and a temperature of 24 degrees Celsius, while a second calibration setting may be used for a pressure of approximately 0.5 atm, a relative humidity level of 10%, and a temperature of 5 degrees Celsius; persons skilled in the art, upon reviewing the entirety of this disclosure, will be aware of various variations in environmental parameters 120 and calibration settings that may be employed. The environmental sensor 128 may include an environmental sensor module as disclosed in U.S. patent application Ser. No. 17/333,169, entitled "SYSTEMS AND METHODS FOR INSPIRATE SENSING TO DETERMINE A PROBABILITY OF AN EMERGENT PHYSIOLOGICAL STATE," filed on May 28, 2021, the entirety of which is incorporated in this disclosure by reference.

Still referring to FIG. 1 apparatus may include a physiological sensor 124, As used in this disclosure, a "physiological sensor" is a device configured to detect a physiological parameter 116 as a function of a physiological state. Physiological sensor 124 may be configured to detect at least a physiological parameter 116 as a function of a physiological state. In some cases, computing device may be further configured to determine at least a user cognitive performance as a function of physiological parameters 116 as described further below. "User cognitive performance," as used in this disclosure is the mental performance of a user. User cognitive performance may be derived from one more or more cognitive statuses determined by computing device as describe described further below. Physiological sensor 124 may include at least a sensor. In an embodiment, sensor may include a baroreceptor, temperature sensor, brain activity sensors, pressure sensors, skin sensors, heart rate sensor, blood pressure sensor, sweat sensor, resistance sensor, voltage sensor, multimeters, and the like. For example, in some cases a sensor may transduce a detected phenomenon, such as without limitation, current, speed, direction, force, torque, moisture, temperature, pressure, geographic location, the physical state of the user, and the like, into a sensed signal. Sensor may include one or more sensors which may be the same, similar, or different. Sensor may include one or more sensor suites with sensors in each sensor suite being the same, similar, or different. Physiological sensor 124 may be configured to detect at least a physiological parameter 116.

Still referring to FIG. 1, at least a physiological sensor 124 may include a hydration sensor; hydration sensor may determine a degree to which a user has an adequate amount of hydration, where hydration is defined as the amount of water and/or concentration of water versus solutes such as electrolytes in water, in a person's body. Hydration sensor may use one or more elements of physiological data, such as sweat content and/or hematological parameters detected without limitation using plethysmography, to determine a degree of hydration of a user; degree of hydration may be associated with an ability to perform under various circumstances. For instance, a person with adequate hydration may be better able to resist the effects of hypoxemia in high-altitude and/or high-G for longer or under more severe circumstances, either because the person's body is better able to respond to causes of hypoxemia and delay onset, or because the person is better able to cope with diminished blood oxygen; this may be true of other conditions and/or physiological states detected using at least a physiological sensor 124, and may be detected using heuristics or relationships derived, without limitation, using machine learning and/or data analysis as set forth in further detail below.

Still referring to FIG. 1, physiological sensor 124 may include a volatile organic compound (VOC) sensor. VOC sensor may sense VOCs, including ketones such as acetone; a user may emit ketones in greater quantities when undergoing some forms of physiological stress, including without limitation hypoglycemia resulting from fasting or overwork, which sometimes results in a metabolic condition known as ketosis. As a result, detections of higher quantities of ketones may indicate a high degree of exhaustion or low degree of available energy; this may be associated with a lessened ability to cope with other physiological conditions and/or parameters that may be detected by or using at least a physiological sensor 124, such as hypoxemia, and/or environmental stressors such as high altitude or G-forces. Such associations may be detected or derived using data analysis and/or machine learning as described in further detail below. In some embodiments, physiological sensor 124 may include an oxygen hose of a mobile respiratory assembly such as a respiration assembly used by a pilot in an aircraft, the sensor array may be configured to detect a gas concentration level. Gas concentration level may include a concentration level of carbon dioxide, which may be sensed directly and/or by detection of a related compound such as H2, where a "related compound" is a compound, whose concentrations may be related mathematically to CO2 concentrations (e.g., they may be proportional to one another). Gas concentration level may include a volatile organic compound (VOC) level. Gas concentration level may include an oxygen level.

Still referring to FIG. 1, at least a physiological parameters 116 may include at least a circulatory parameter, which may include any detectable parameter describing the state of blood vessels such as arteries, veins, or capillaries, any datum describing the rate, volume, pressure, pulse rate, or other state of flow of blood or other fluid through such blood vessels, chemical state of such blood or other fluid, or any other parameter relative to health or current physiological state of user as it pertains to the cardiovascular system. As a non-limiting example, at least a circulatory parameter may include a blood oxygenation level of user's blood. At least a circulatory parameter may include a pulse rate. At least a circulatory parameter may include a blood pressure level. At least a circulatory parameter may include heart rate variability and rhythm. At least a circulatory parameter may include a plethysmograph describing user blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse oxygen level (for instance by detecting plethysmograph amplitude), pulse rate (for instance by detecting plethysmograph frequency), heart rate variability and rhythm (for instance by tracking pulse rate and other factors over time), and blood pressure, among other things.

Still referring to FIG. 1, at least a physiological parameter 116 may include neural oscillations generated by user neurons, including without limitation neural oscillations detected in the user's cranial region, sometimes referred to as "brainwaves." Neural oscillations include electrical or magnetic oscillations generated by neurological activity, generally of a plurality of neurons, including superficial cranial neurons, thalamic pacemaker cells, or the like. Neural oscillations may include alpha waves or Berger's waves, characterized by frequencies on the order of 7.5-12.5 Hertz, beta waves, characterized by frequencies on the order of 13-30 Hertz, delta waves, having frequencies ranging from 1-4 Hertz, theta waves, having frequencies ranging from 4-8 Hertz, low gamma waves having frequencies from 30-70 Hertz, and high gamma waves, which have frequencies from 70-150 Hertz. Neurological oscillations may be associated with degrees of wakefulness, consciousness, or other neurological states of user, for instance as described in further detail below. At least a sensor may detect body temperature of at least a portion of user's body, using any suitable method or component for temperature sensing.

Still referring to FIG. 1, physiological sensor 124 may be configured to measure a plurality of physiological parameters 116 of a user, wherein the plurality of physiological parameters 116 comprises at least a plurality of blood-oxygenation signals as described above (e.g., circulatory parameter, gas concentration, VOC). In some embodiments physiological sensor 124 may include a near-IR spectroscopy sensor. In some embodiments, near-IR spectroscopy sensor may be configured to measure cranial blood-oxygenation signals from the user. The near-infrared spectroscopy sensor may include at least one optical sensor and at least one infrared light emitting diode. Physiological sensor 124 may include a cranial blood oxygen sensor, for example as described in U.S. patent application Ser. No. 17/859,483, entitled "HUMAN PERFORMANCE OXYGEN SENSOR," filed on Apr. 27, 2020, the entirety of which is incorporated in this disclosure by reference. Another exemplary physiological sensor 124 may include an exhalation sensor, for example as described in U.S. patent Ser. No. 11/172,845, entitled "COMBINED EXHALED AIR AND ENVIRONMENTAL GAS SENSOR APPARATUS," filed Jul. 20, 2020, the entirety of which is incorporated in this disclosure by reference. Yet another exemplary, physiological sensor 124 may include an inhalation sensor, for example as described in U.S. patent application Ser. No. 17/333,179, entitled "INHALATION SENSOR APPARATUS FOR MOBILE RESPIRATION EQUIPMENT," filed on May 28, 2021, the entirety of which is incorporated in this disclosure by reference.

Still referring to FIG. 1, in some embodiments, apparatus 100 may include at least a cutaneous sensor 132 that includes a skin galvanic sensor. Skin galvanic sensor may be configured to detect a skin galvanic response as a function of a cutaneous electrical characteristic. As used in the current disclosure, "galvanic skin response" (GSR) is a cutaneous phenomenon that causes variation in the electrical characteristics of the skin or the cutaneous phenomenon's representation as a cutaneous parameter. GSR may also refer to a recorded electrical resistance between two electrodes when a very weak current is steadily passed between them. GSR may also be referred to as skin conductance, galvanic skin response (GSR), electrodermal response (EDR), psychogalvanic reflex (PGR), skin conductance response (SCR), sympathetic skin response (SSR), and skin conductance level (SCL). Under GSR, skin resistance may vary with the state of sweat glands in the skin. Sweating may be controlled by the sympathetic nervous system, and skin conductance may be an indication of psychological or physiological arousal. If a sympathetic branch of an autonomic nervous system is highly aroused, then sweat gland activity may increase. This in turn increases skin conductance. In this way, skin conductance may be a measure of emotional and sympathetic responses. GSR may represent a relationship between emotional arousal and sympathetic activity, although electrical change alone may not identify which specific emotion is being elicited. These autonomic sympathetic changes may alter sweat and blood flow, which in turn affects GSR. The number of sweat glands varies across the human body, being highest in hand and foot regions. In some embodiments cutaneous sensor 132 may account for the number of sweat glands that are present in a given area. The response of the skin and muscle tissue to external and internal stimuli can cause conductance to vary by several microsiemens. Sensor may detect, transmit, record and/or display these subtle changes. In other embodiments, a galvanic skin sensor may be configured to detect changes between electrodermal resistance and electrodermal potential. A galvanic skin sensor may use a plurality of electrodes; the electrodes may be placed about a distance apart (e.g., an inch apart). In some embodiments, galvanic skin sensor may measure electrodermal resistance between plurality of electrodes. In some embodiments, galvanic skin sensor may measure electrodermal potential between plurality of electrodes. In some embodiments, galvanic skin sensor may measure electrodermal current between plurality of electrodes. In some embodiments, resistance measured by galvanic skin sensor may vary according to emotional state of user. In other embodiments, a galvanic skin sensor may further be configured to detect Galvanic skin potential (GSP). GSP refers to potential (e.g., voltage) measured between two electrodes without any externally applied current. GSP may be measured by connecting electrodes to an amplifier. In some cases, GSP may vary with the emotional state of the subject.

With continued reference to FIG. 1, physiological sensor 124 may include at least an eye sensor 134. As used in this disclosure, an "eye sensor" is any system or device that is configured or adapted to detect an eye parameter as a function of an eye phenomenon. In some cases, at least an eye sensor 134 may be configured to detect at least an eye parameter as a function of at least an eye phenomenon. As used in this disclosure, an "eye parameter" is an element of information associated with an eye. Exemplary non-limiting eye parameters may include blink rate, eye-tracking parameters, pupil location, gaze directions, pupil dilation, and the like. Exemplary eye parameters are described in greater detail below. In some cases, an eye parameter may be transmitted or represented by an eye signal. An eye signal may include any signal described in this disclosure. As used in this disclosure, an "eye phenomenon" may include any observable phenomenon associated with an eye, including without limitation focusing, blinking, eye-movement, and the like. Eye sensor 134 may include any sensor described in this disclosure, including with reference to FIG. 2 below. In some embodiments, at least an eye sensor 134 may include an electromyography sensor. Electromyography sensor may be configured to detect at least an eye parameter as a function of at least an eye phenomenon.

Still referring to FIG. 1, in some embodiments, eye sensor 134 may include an optical eye sensor 134. Optical eye sensor 134 may be configured to detect at least an eye parameter as a function of at least an eye phenomenon. In some cases, an optical eye sensor 134 may include a camera directed toward one or both of user's eyes. In some cases, optical eye sensor 134 may include a light source, likewise directed to user's eyes. Light source may have a non-visible wavelength, for instance infrared or near-infrared. In some cases, a wavelength may be selected which reflects at an eye's pupil (e.g., infrared). Light that selectively reflects at an eye's pupil may be detected, for instance by camera. Images of eyes may be captured by camera. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object (e.g., user or person's eyes). In some cases, image data may be generated by a camera. "Image data" may be used interchangeably through this disclosure with "image," where image is used as a noun. An image may be optical, such as without limitation where at least an optic is used to generate an image of an object 108. An image may be material, such as without limitation when film is used to capture an image. An image may be digital, such as without limitation when represented as a bitmap. Alternatively, an image may be comprised of any media capable of representing a physical scene, space, and/or object 108. Alternatively where "image" is used as a verb, in this disclosure, it refers to generation and/or formation of an image.

Still referring to FIG. 1, an exemplary camera is an OpenMV Cam H7 from OpenMV, LLC of Atlanta, Georgia, U.S.A. OpenMV Cam includes a small, low power, microcontroller which allows execution of processes. OpenMV Cam comprises an ARM Cortex M7 processor 108 and a 640×480 image sensor operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detect motion, for example by way of frame differencing algorithms; detect markers, for example blob detection; detect objects, for example face detection; track eyes; detection persons, for example by way of a trained machine learning model; detect camera motion, for example by way of optical flow detection; detect and decode barcodes; capture images; and record video.

Still referring to FIG. 1, in some cases, a camera may be used to determine eye patterns (e.g., track eye movements). For instance, camera may capture images and processor 108 (internal or external) to camera may process images to track eye movements. In some embodiments, a video-based eye tracker may use corneal reflection (e.g., first Purkinje image) and a center of pupil as features to track over time. A more sensitive type of eye-tracker, a dual-Purkinje eye tracker, may use reflections from a front of cornea (i.e., first Purkinje image) and back of lens (i.e., fourth Purkinje image) as features to track. A still more sensitive method of tracking may include use of image features from inside eye, such as retinal blood vessels, and follow these features as the eye rotates. In some cases, optical methods, particularly those based on video recording, may be used for gaze-tracking and may be non-invasive and inexpensive.

Still referring to FIG. 1, for instance, in some cases a relative position between camera and user may be known or estimable. Pupil location may be determined through analysis of images (either visible or infrared images). In some cases, camera may focus on one or both eyes and record eye movement as viewer looks. In some cases, eye-tracker may use center of pupil and infrared/near-infrared non-collimated light to create corneal reflections (CR). A vector between pupil center and corneal reflections can be used to compute a point of regard on surface (i.e., a gaze direction). In some cases, a simple calibration procedure with an individual user may be needed before using an optical eye tracker. In some cases, two general types of infrared/near-infrared (also known as active light) eye-tracking techniques can be used: bright-pupil (light reflected by pupil) and dark-pupil (light not reflected by pupil). Difference between bright-pupil and dark pupil images may be based on a location of illumination source with respect to optics. For instance, if illumination is coaxial with optical path, then eye may act as a retroreflector as the light reflects off retina creating a bright pupil effect similar to red eye. If illumination source is offset from optical path, then pupil may appear dark because reflection from retina is directed away from camera. In some cases, bright-pupil tracking creates greater iris/pupil contrast, allowing more robust eye-tracking with all iris pigmentation, and greatly reduces interference caused by eyelashes and other obscuring features. In some cases, bright-pupil tracking may also allow tracking in lighting conditions ranging from total darkness to very bright.

Still referring to FIG. 1, alternatively, in some cases, a passive light optical eye tracking method may be employed. Passive light optical eye tracking may use visible light to illuminate. In some cases, passive light optical tracking yields less contrast of pupil than with active light methods; therefore, in some cases, a center of iris may be used for calculating a gaze vector. In some cases, a center of iris determination requires detection of a boundary of iris and sclera (e.g., limbus tracking). In some case, eyelid obstruction of iris and our sclera may challenge calculations of an iris center.

Still referring to FIG. 1, some optical eye tracking systems may be head-mounted, some may require the head to be stable, and some may function remotely and automatically track the head during motion. Optical eye tracking systems may capture images at frame rate. Exemplary frame rates include 15, 30, 60, 120, 240, 350, 1000, and 1250 Hz.

With continued reference to FIG. 1, physiological sensor 124 may include at least a speech sensor. As used in this disclosure, a "speech sensor" is any system or device that is configured or adapted to detect a speech parameter as a function of a speech phenomenon. In some cases, speech sensor may be configured to detect at least a speech parameter as a function of at least a speech phenomenon. As used in this disclosure, a "speech parameter" is an element of information associated with speech. An exemplary non-limiting speech parameter is a representation of at least a portion of audible speech, for instance a digital representation of audible speech. In some cases, a speech parameter may be transmitted or represented by a speech signal. A speech signal may include any signal described in this disclosure. As used in this disclosure, a "speech phenomenon" may include any observable phenomenon associated with speech, including without limitation audible phenomena and/or acoustic phenomena. Speech phenomena may include pressure changes, for instance audible pressure changes as detectable by a microphone. In some cases, speech phenomenon may not be directly related to speech, and may include phenomena related to breathing. For example, breathing sounds may be detected by speech sensor and used as speech parameter. Speech sensor may include any sensor described in this disclosure. In some embodiments, at least a speech sensor may include a bone conductance transducer. In some cases, bone conductance transducer may be configured to detect at least a speech parameter as a function of at least a speech phenomenon. In some cases, apparatus 100 may utilize communication signals and use them as representation of speech parameters 124. For instance, in some cases, a user may already be in audible communication with others, through communication microphones.

Still referring to FIG. 1, in some cases, speech sensor may include a microphone, for example an air spaced microphone. In some cases, microphone may be configured to detect at least a speech parameter as a function of at least a speech phenomenon. In some cases, speech phenomenon may include sound or sounds associated with speech, i.e., oral verbalization. As used in this disclosure, a "microphone" is any transducer configured to transduce pressure change phenomenon to a signal, for instance a signal representative of a parameter associated with the phenomenon. Microphone, according to some embodiments, may include a transducer configured to convert sound into an audio signal. Exemplary non-limiting microphones include dynamic microphones (which may include a coil of wire suspended in a magnetic field), condenser microphones (which may include a vibrating diaphragm condensing plate), and a contact (or conductance) microphone (which may include piezoelectric crystal material). Microphone may include any microphone for transducing pressure changes, as described above; therefore, microphone may include any variety of microphone, including any of: condenser microphones, electret microphones, dynamic microphones, ribbon microphones, carbon microphones, piezoelectric microphones, fiber-optic microphones, laser microphones, liquid microphones, microelectromechanical systems (MEMS) microphones, and/or a speaker microphone. An "audio signal," as used in this disclosure, is a representation of sound. In some cases, an audio signal may include an analog electrical signal of time-varying electrical potential. In some embodiments, an audio signal may be communicated (e.g., transmitted and/or received) by way of an electrically transmissive path (e.g., conductive wire), for instance an audio signal path. Alternatively or additionally, audio signal may include a digital signal of time-varying digital numbers. In some cases, a digital audio signal may be communicated (e.g., transmitted and/or received) by way of any of an optical fiber, at least an electrically transmissive path, and the like. In some cases, a line code and/or a communication protocol may be used to aid in communication of a digital audio signal. Exemplary digital audio transports include, without limitation, Alesis Digital Audio Tape (ADAT), Tascam Digital Interface (TDIF), Toshiba Link (TOSLINK), Sony/Philips Digital Interface (S/PDIF), Audio Engineering Society standard 3 (AES3), Multichannel Audio Digital Interface (MADI), Musical Instrument Digital Interface (MIDI), audio over Ethernet, and audio over IP. Audio signals may represent frequencies within an audible range corresponding to ordinary limits of human hearing, for example substantially between about 20 and about 20,000 Hz. According to some embodiments, an audio signal may include one or more parameters, such as without limitation bandwidth, nominal level, power level (e.g., in decibels), and potential level (e.g., in volts). In some cases, relationship between power and potential for an audio signal may be related to an impedance of a signal path of the audio signal. In some cases, a signal path may single-ended or balanced.

Still referring to FIG. 1, computing device is configured to receive physiological feedback 136 and environmental feedback 140 from the plurality of sensors. Computing device may be communicatively connected to the plurality of sensors described throughout this disclosure. Computing device 104 may communicate with a sensor using any method, including by way of communication signals. As used in this disclosure, a "signal" is any intelligible representation of data, for example from one device to another. A signal may include an optical signal, a hydraulic signal, a pneumatic signal, a mechanical, signal, an electric signal, a digital signal, an analog signal and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like. In some embodiments, the plurality of sensors describe herein may transmit physiological parameters and environmental parameters, wherein processor 108 receives the signals as physiological feedback and environmental feedback. "Physiological feedback," as used in this disclosure, is a plurality of physiological parameters transmitted from a sensor. "Environmental feedback," as used in this disclosure, is a plurality of environmental parameters transmitted from a sensor.

Still referring to FIG. 1, in some embodiments, computing device may determine a cognitive status of a user as a function of physiological feedback 136. As used in this disclosure, "cognitive status" is a representation of mental performance. Exemplary cognitive statuses may include classifications, for instance impaired or unimpaired. Alternatively or additionally, cognitive status may include a relative or absolute continuously variable measure that indicates performance. For example, cognitive status may be represented as a proportion or percentage relative an ideal or satisfactory cognitive performance. Cognitive performance can be pegged relative a user's performance. Alternatively or additionally, in some cases, cognitive performance may be pegged relative a level of cognitive performance required for a given task or responsibility.

Still referring to FIG. 1, in some embodiments, processor 108 may be configured to determine a cognitive status by using one or more machine learning processes as described further below. In some cases, processor 108 may receive cognitive status training data. As used in this disclosure, "cognitive status training data" is a training set that correlates behavioral parameters, such as without limitation physiological parameters 116, to cognitive statuses. In some cases, cognitive status training data may be compiled and/or correlated from historic information, for instance by a user. In some cases, cognitive status training data may be compiled and/or correlated by an unsupervised machine learning process. Cognitive status training data may use physiological parameters 116 correlated to cognitive status for one individual user, or for a cohort or population of users. Historic information may include information from cognitive status-related study. In some cases, historical information may include information captured from use of apparatus 100. Processor 108 may input cognitive status training data into a cognitive status machine learning algorithm, such as a classifier as described further below. As used in this disclosure, an "cognitive status machine learning algorithm" is any machine learning algorithm that is configured to train a cognitive status machine learning model using cognitive status training data. Processor 108 may train a cognitive status machine learning model, as a function of the cognitive status machine learning algorithm. As used in this disclosure, "cognitive status machine learning model" is a machine learning model that is configured to take as input physiological parameters 116, such as without limitation eye patterns, eye parameters, speech patterns, and speech parameters, and output at least a correlated cognitive status. Processor 108 may determine cognitive status as a function of cognitive status machine learning model and one or more of at least an eye pattern and the least a speech pattern. Still referring to FIG. 1, computing device 104 is configured to generate an external factor profile 148 containing a plurality of external factors selected by the processor 108 configured to improve the user cognitive performance as a function of the received biological feedback and environmental feedback. An "external factor," as used in this disclosure, is a parameter external to a user. An external factor may include environmental factors, equipment connected to computing device, and the like. An "external factor profile," as used in this disclosure, is a data structure containing analytical data regarding the effect of external factors on user cognitive performance. For example, external factor profile 148 may correlate the effect of cabin pressure on a user's oxygen inhalation levels. External factor profile 148 may include instructions to modify external factors. This may include the increase or decrease of environmental parameters 120, such as environment temperature. Modifications may also include maintenance of equipment in contact with the user. In some embodiments, computing device 104 may use a classifier to categorize the effects of the plurality of external factors on user cognitive performance. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. Classifier 144 may be configured to output at least a datum that labels or otherwise identifies a set of data that are clustered together, found to be close under a distance metric as described below, or the like. Computing device and/or another device may generate classifier 144 using a classification algorithm, defined as a processes whereby computing device derives a classifier 144 from training data. For example, classifier 144 may output a plurality of data bins categorized by a cognitive status, physiological and/or environmental conditions such as hypoxemia, high altitude or G-forces, and the like. In some embodiments, computing device 104 may train classifier 144 to intake physiological feedback 136 and environmental feedback 140 as inputs. Training data may include historic information, a plurality of cognitive statutes, physiological feedback 136, environmental feedback, and the like. In some embodiments, training data may be classified for example, by user, by user cohort, or the like. In some cases, a typical user value may include a user value matched to one or more demographic facts about user. For instance, a pulse rate associated with loss of consciousness in a first cohort may not be associated with loss of consciousness in a second cohort, or vice-versa; where user is the first cohort, the former pulse rate may be used as a baseline value for pulse rate. Baseline value may similarly be selected using a typical value for persons matching user's age, sex, height, weight, degree of physical fitness, physical test scores, ethnicity, diet, or any other suitable parameter. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Still referring to FIG. 1, computing device 104 may use the outputs of classifier 144 to compare the effects of external factors on user cognitive performance and select external factors that improves user cognitive performance. For example, computing device 104, may use a knowledge-based system (KBS) to select and generate external factor profile 148. As used in this disclosure, a "KBS" is a computer program that reasons and uses a knowledge base to solve complex problems. The KBS has two distinguishing features: a knowledge base and an inference engine. A knowledge base may include technology used to store complex structured and unstructured information used by a computer system. Other common approaches in addition to a subsumption ontology include frames, conceptual graphs, and logical assertions. In some embodiments, the knowledge base may be a storage hub that contains information about past external facto profiles, feedback from about the effect of the external factor profile in improving user cognitive performance, a plurality of common and/or experimental solution to a physiological condition, and the like. Next, an inference engine may allow new knowledge to be inferred regarding classifier 144 outputs. For example, the inference engine may infer, as a function of classifier 144, that the environmental gas levels of a cabin is correlated to a physiological condition such as hypoxia in a user and negatively affecting user cognitive performance. The inference engine may then derive modifications to an external factor, such as increasing gas levels to reduce or reverse the physiological condition and improve user cognitive performance. Inference may take the form of IF-THEN rules coupled with forward chaining or backward chaining approaches. Forward chaining starts with the known facts and asserts new facts. Backward chaining starts with goals and works backward to determine what facts must be asserted so that the goals can be achieved. Other approaches include the use of automated theorem provers, logic programming, blackboard systems, and term rewriting systems such as CHR (Constraint Handling Rules). The inference engine may make predictions or decisions in improving user cognitive performance without being explicitly programmed to do so. The inference engine may receive constant feedback and self-learn based on previous classifications, as described through this disclosure. Computing device may utilize classifier 144 in combination with the KBS to generate external factor profile 148.

Still referring to FIG. 1, computing device 104 may be configured to generate classifier 144 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate classifier 144 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l = \sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, external factor profile may include an alert. As used in this disclosure, an "alert" is a communication to a flight crew member. In some cases, an alert may indicate a warning pertaining to a flight crew member's risk of atelectasis. An alert may be communicated audibly, visually, and/or haptically. In some cases, alert may include a message. As used in this disclosure, a "message" is a communication configured to communicate information. For example, in some cases, a message may communicate a procedure which a user should engage in. Alternatively or additionally, a message may communicate a warning to a user about diminished performance. A message may be communicated visually, audibly, and/or haptically. As used in this disclosure, a "user interface" is a system that is designed and/or configured to facilitate communication between at least a system, such as without limitation a computing device, and a user by way of at least an output communicated to the user and/or at least an input communicated from the user. Exemplary non-limiting user interfaces include displays, audio systems, haptic systems, head mounted displays, mice, joysticks, keyboards, and the like.

Figure 2:
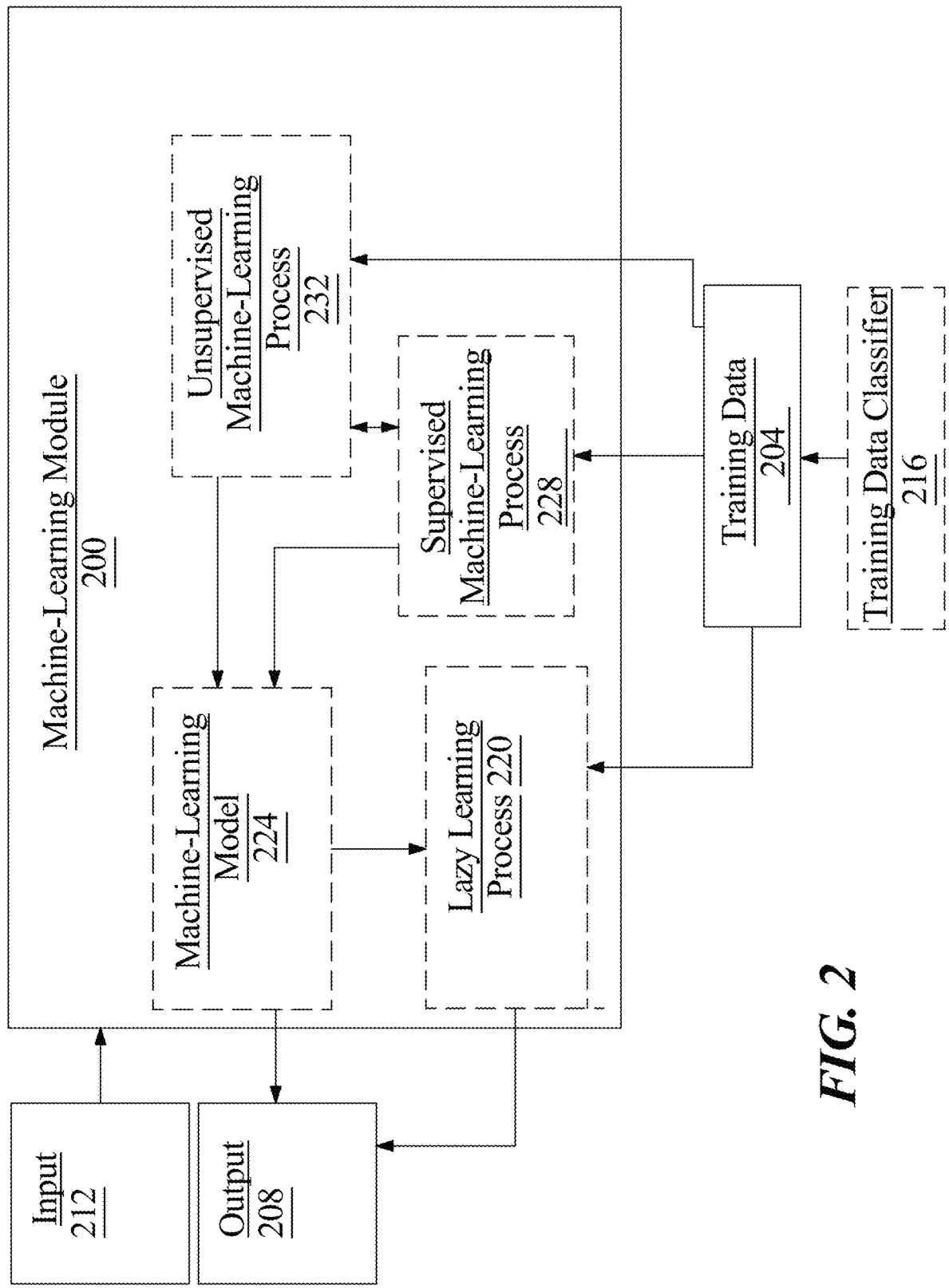
FIG. 2 an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device 104/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device 104 and/or any module and/or component operating thereon derives a classifier from training data 204. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory 112; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs, as described above, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the LASSO model is the Frobenius norm amounting to the square root of the sum of squares of all terms. Linear regression models may include the elastic net model, a multi-task elastic net model, a least angle regression model, a LARS LASSO model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 3:
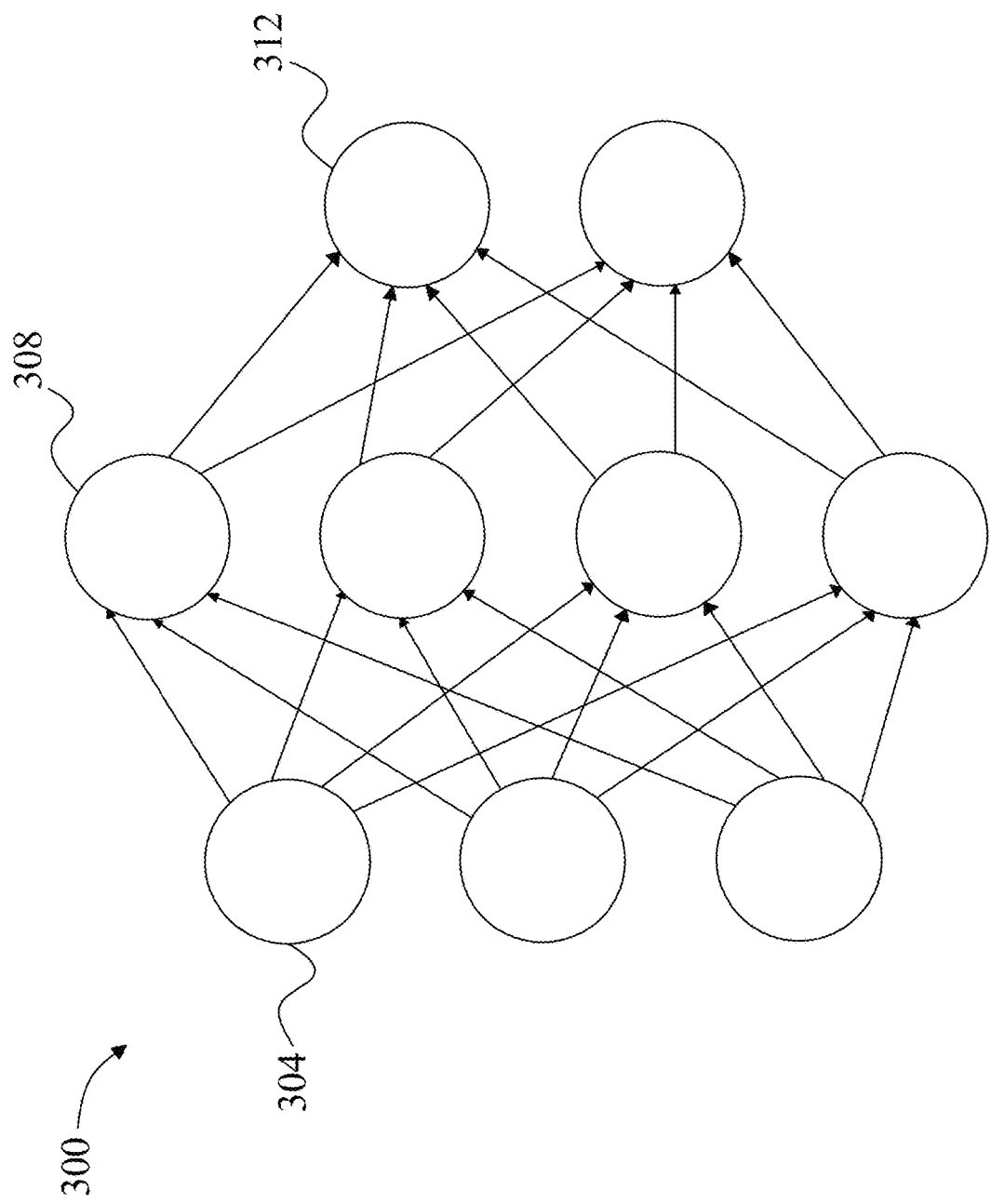
FIG. 3 an exemplary embodiment of neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
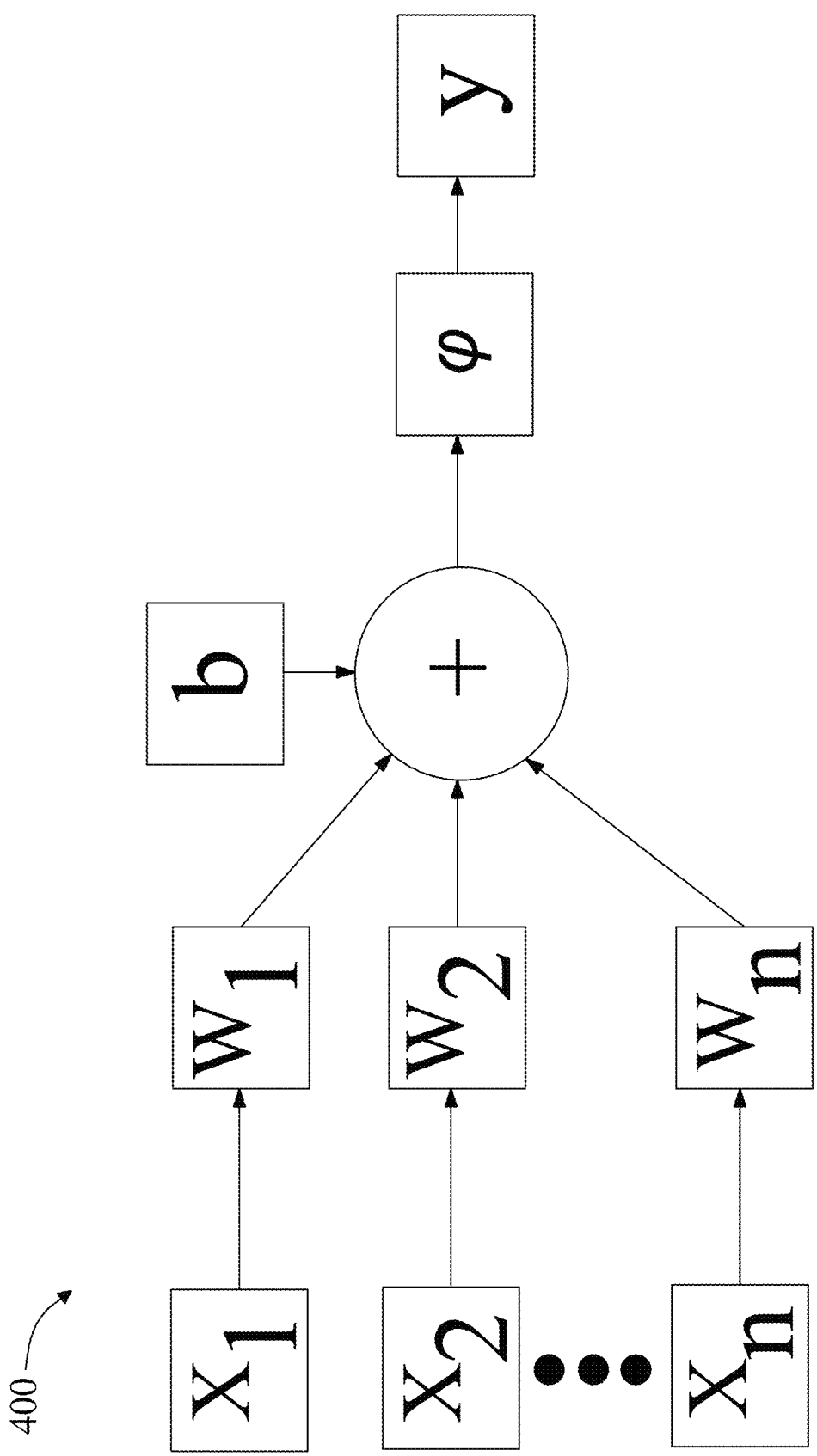
FIG. 4 is a diagram of an exemplary embodiment of a node of a neural network.

Referring now to FIG. 4, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function ω, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight.

Figure 5:
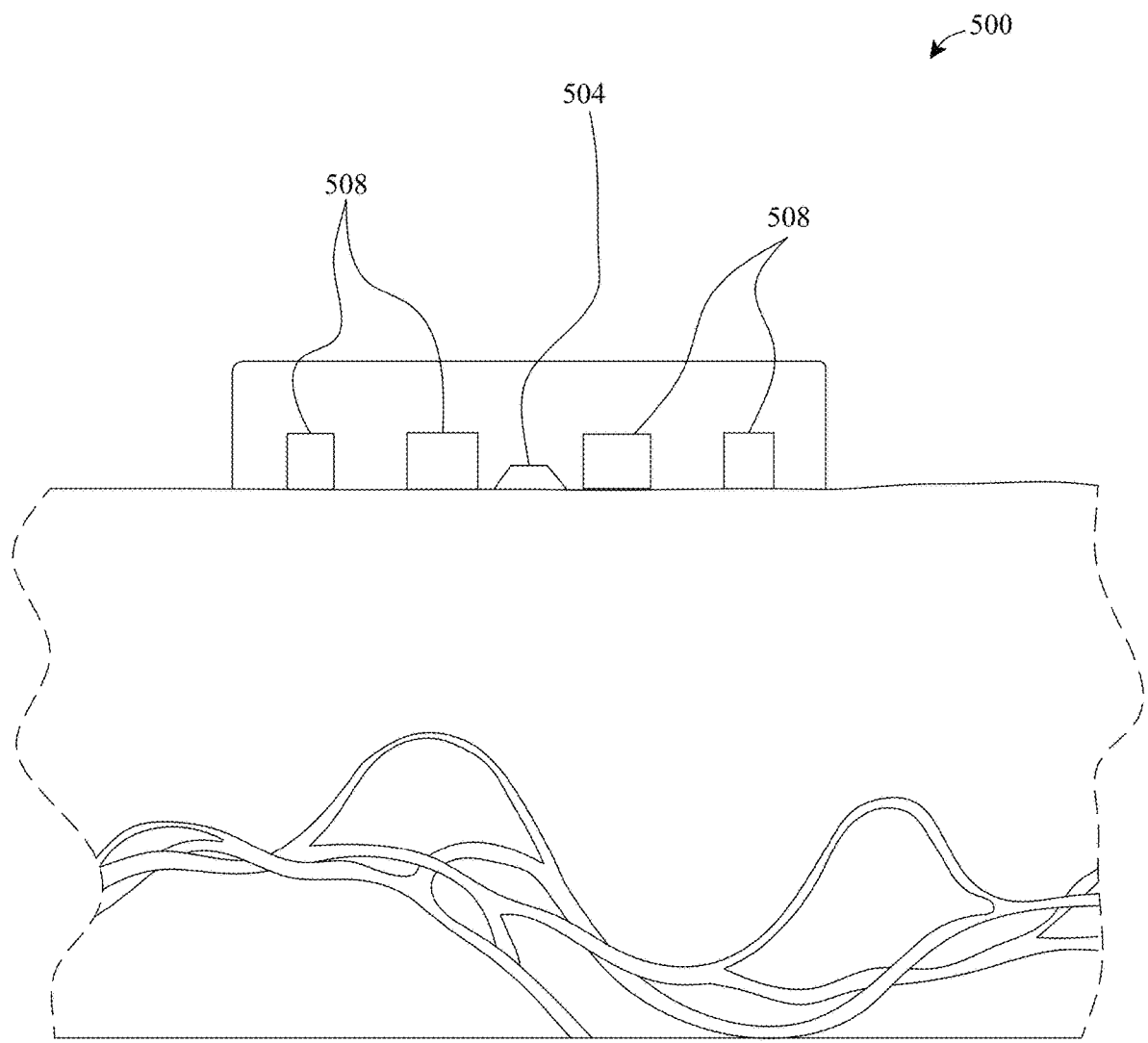
FIG. 5 is a schematic illustration of an exemplary embodiment of a near-infrared spectroscopy sensor.

Referring now to FIG. 5, at least a physiological sensor 124 may include an optical sensor, which detects light emitted, reflected, or passing through human tissue. Optical sensor may include a near-infrared spectroscopy sensor (NIRS). A NIRS, as used herein, is a sensor that detects signals in the near-infrared electromagnetic spectrum region, having wavelengths between 780 nanometers and 2,400 nanometers. FIG. 5 illustrates an exemplary embodiment of a NIRS 500 against an exterior body surface, which may include skin. NIRS 500 may include a light source 505, which may include one or more light-emitting diodes (LEDs) or similar element. Light source 505 may, as a non-limiting example, convert electric energy into near-infrared electromagnetic signals. Light source 505 may include one or more lasers. NIRS 500 may include one or more detectors 508 configured to detect light in the near-infrared spectrum. Although the wavelengths described herein are infrared and near-infrared, light source 505 may alternatively or additionally emit light in one or more other wavelengths, including without limitation blue, green, ultraviolet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation $CO_2$ saturation levels, state of hemoglobin as opposed to blood oxygen saturation generally. One or more detectors 508 may include, without limitation, charge-coupled devices (CCDs) biased for photon detection, indium gallium arsenide (InGaAs) photodetectors, lead sulfide (PbS) photodetectors, or the like. NIRS 500 may further include one or more intermediary optical elements (not shown), which may include dispersive elements such as prisms or diffraction gratings, or the like. In an embodiment, NIRS 500 may be used to detect one or more circulatory parameters, which may include any detectable parameter further comprises at least a circulatory parameter.

Figure 6:
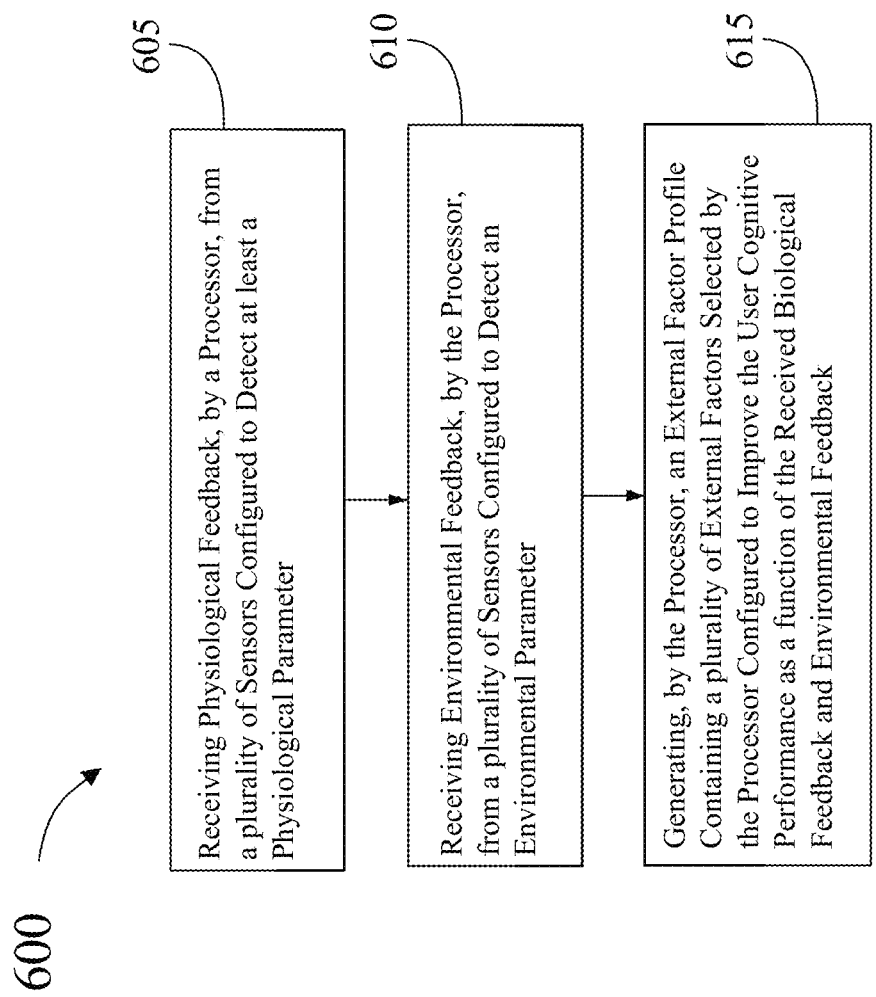
FIG. 6 is flow diagram of an exemplary method gauging the effect of external factors relating to a user cognitive performance.

Referring now to FIG. 6, is a flow diagram of an exemplary method 600 for gauging the effect of external factors relating to a user cognitive performance. At step 605, method 600 includes receiving physiological feedback, by a processor, from a plurality of sensors configured to detect at least a physiological parameter, as implemented and with reference to FIGS. 1-5. In some embodiments, a sensor of the plurality of sensors may include a physiological sensor such as a near-IR spectroscopy sensor, a cutaneous sensor, an environmental sensor, an eye senor configured to detect and eye parameter as a function of an eye phenomenon, and/or the like.

Still referring to FIG. 1, at step 610, method 600 includes receiving environmental feedback, by the processor, from a plurality of sensors configured to detect an environmental parameter as implemented and with reference to FIGS. 1-5.

Still referring to FIG. 1, at step 615 method 600 includes generating, by the processor, an external factor profile containing a plurality of external factors selected by the processor configured to improve the user cognitive performance as a function of the received biological feedback and environmental feedback, as implemented and with reference to FIGS. 1-5. In some embodiments, generating the external factor profile may include, generating, by the processor a cognitive status related to the user. In some embodiments, generating the external factor may include determining, by the processor, an effect a plurality of external factors have on the user cognitive performance. In some embodiments, the external factor profile may include an alert. In some embodiments, generating, by the processor, the external factor profile may include training a machine-learning model to generate a classifier configured to output the external factor profile.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
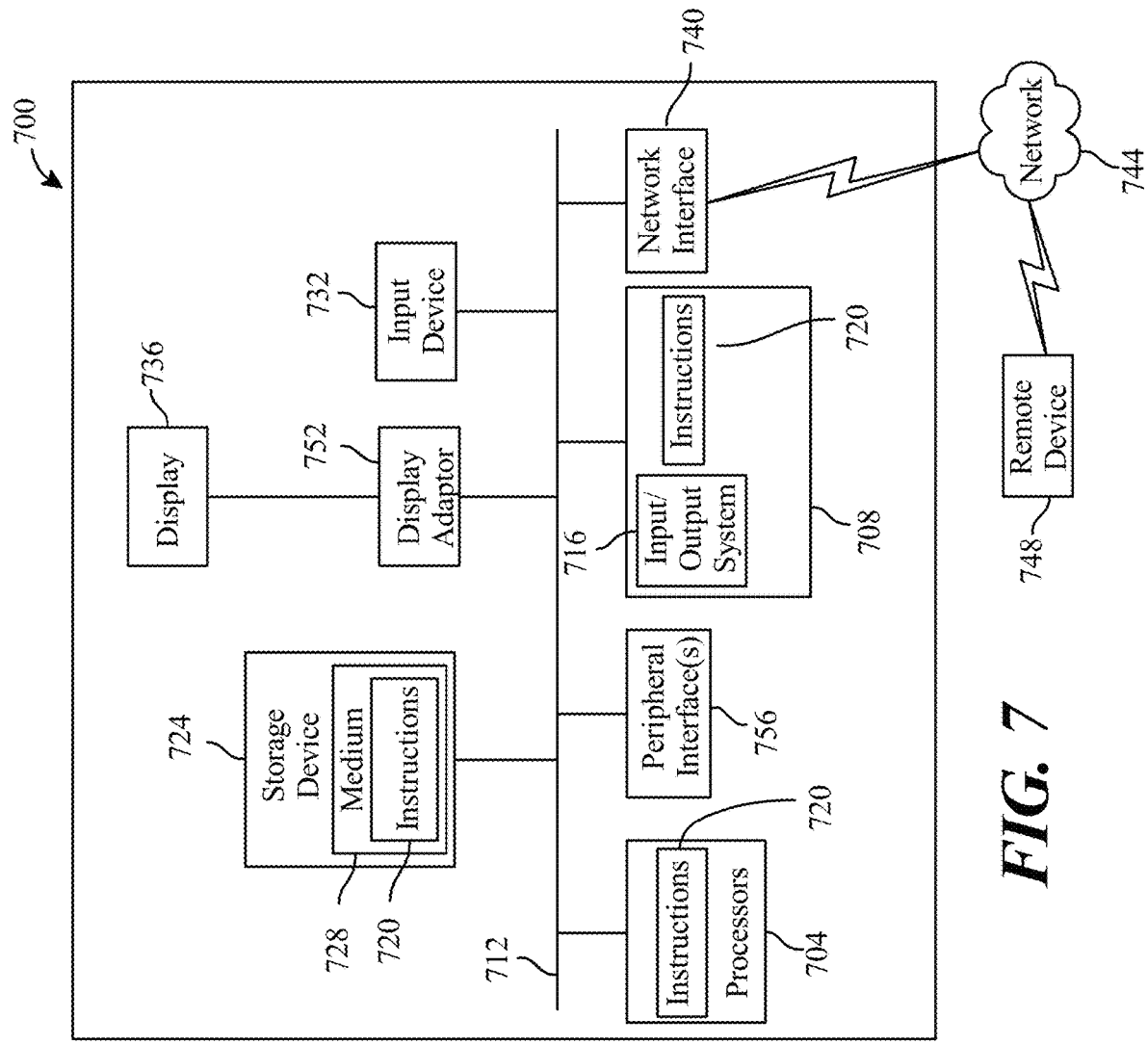
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatuses, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for gauging an effect of external factors relating to a user cognitive performance, the apparatus comprising:
   a plurality of sensors configured to detect at least a physiological parameter and an environmental parameter;
   at least one processor; and
   a memory communicatively connected to the at least a processor, the memory containing instructions configuring the at least a processor to:
      determine a calibration setting as a function of comparing the at least an environmental parameter to a range of value;
      receive physiological feedback from the plurality of sensors;
      receive environmental feedback from the plurality of sensors;
      determine a cognitive status as a function of the physiological feedback, wherein determining the cognitive status further comprises:
         receiving cognitive status training data correlating behavioral parameter inputs to cognitive status outputs;
         training a cognitive status machine-learning model using the cognitive status training data;
         determining the cognitive status as a function of the trained cognitive status machine-learning model and one or more of at least an eye pattern and at least a speech pattern;
      generate an external factor profile comprising a plurality of external factors,
      wherein the external factor profile comprises instructions to modify the plurality of external factors wherein an external factor of the plurality of external factors comprises at least an environment temperature, wherein:
         the external factor profile is configured to improve a user cognitive performance as a function of the trained cognitive status machine-learning model, the received physiological feedback and environmental feedback; and
         generating the external factor profile comprises:
            iteratively training a machine-learning model with training data classified to a user cohort matched to demographic facts about a user;
            categorizing, using the machine-learning model, effects of the plurality external factors on user cognitive performance based on cognitive statues determined using the trained cognitive status machine-learning model; and
            generating, as a function of the categorization, using a knowledge-based system, modifications to the plurality of external factors.

2. The apparatus of claim 1, wherein the plurality of sensors comprises a physiological sensor.

3. The apparatus of claim 2, wherein the physiological sensor comprises a comprises a near-IR spectroscopy sensor.

4. The apparatus of claim 1, wherein the plurality of sensors comprises a cutaneous sensor.

5. The apparatus of claim 1, wherein the plurality of sensors comprises an environmental sensor.

6. The apparatus of claim 1, wherein the plurality of sensors comprises an eye sensor configured to detect an eye parameter as a function of an eye phenomenon.

7. The apparatus of claim 1, wherein the memory contains instructions further configuring the at least one processor to generate a cognitive status related to the user, utilizing a classification algorithm.

8. The apparatus of claim 1, wherein generating the external factor comprises determining an effect of the plurality of external factors have on the user cognitive performance.

9. The apparatus of claim 1, wherein the external factor profile comprises an alert.

10. A method for gauging an effect of external factors relating to a user cognitive performance, the method comprising:
   receiving physiological feedback, by a processor, from a plurality of sensors configured to detect at least a physiological parameter;
   receiving environmental feedback, by the processor, from the plurality of sensors configured to detect an environmental parameter; and
   comparing, by the processor, the at least an environmental parameter to a range of values associated with a plurality of calibration settings;
   determining, by a processor, one calibration setting from the plurality of calibration settings based on the comparing of the at least an environmental parameter to the range of values;
   determine a cognitive status as a function of the physiological feedback, wherein determining the cognitive status further comprises:
      receiving cognitive status training data correlating behavioral parameter inputs to cognitive status outputs;
      training a cognitive status machine-learning model using the cognitive status training data;
      determining the cognitive status as a function of the trained cognitive status machine-learning model and one or more of at least an eye pattern and at least a speech pattern;
   generating, by the processor, an external factor profile comprising a plurality of external factors selected by the processor configured to improve the user cognitive performance as a function of the trained cognitive status machine-learning model, the received physiological feedback and environmental feedback, wherein the external factor profile comprises instructions to modify the plurality of external factors wherein an external factor of the plurality of external factors comprises at least an environment temperature, wherein generating the external factor profile comprises:
      iteratively training a machine-learning model with training data classified to a user cohort matched to demographic facts about a user;

categorizing, using the machine-learning model, effects of the plurality external factors on user cognitive performance based on cognitive statuses determined using the trained cognitive status machine-learning model; and generating, as a function of the categorization, using a knowledge-based system, modifications to the plurality of external factors.

11. The method of claim 10, wherein the plurality of sensors comprises a physiological sensor.

12. The method of claim 11, wherein the physiological sensor comprises a comprises a near-IR spectroscopy sensor.

13. The method of claim 10, wherein the plurality of sensors comprises a cutaneous sensor.

14. The method of claim 10, wherein the plurality of sensors comprises an environmental sensor.

15. The method of claim 10, wherein the plurality of sensors comprises an eye sensor configured to detect an eye parameter as a function of an eye phenomenon.

16. The method of claim 10, wherein generating the external factor profile further comprises, generating, by the processor a cognitive status related to the user, utilizing a classification algorithm.

17. The method of claim 10, wherein generating the external factor comprises determining, by the processor, an effect the plurality of external factors have on the user cognitive performance.

18. The method of claim 10, wherein the external factor profile comprises an alert.

\* \* \* \* \*